United States Patent
Chauvet et al.

(10) Patent No.: US 6,648,880 B2
(45) Date of Patent: Nov. 18, 2003

(54) METHOD OF USING CRYOTREATMENT TO TREAT BRAIN TISSUE

(75) Inventors: Patrick Chauvet, St-Laurent (CA); Daniel Nahon, Ottawa (CA)

(73) Assignee: CryoCath Technologies Inc., Kirkland (CA)

(*) Notice: Subject to any disclaimer, the term of this patent is extended or adjusted under 35 U.S.C. 154(b) by 0 days.

(21) Appl. No.: 10/077,183

(22) Filed: Feb. 15, 2002

(65) Prior Publication Data

US 2002/0128638 A1 Sep. 12, 2002

Related U.S. Application Data

(60) Provisional application No. 60/269,566, filed on Feb. 16, 2001.

(51) Int. Cl.[7] ............................................. A61B 18/18
(52) U.S. Cl. ............................................. 606/21; 606/23
(58) Field of Search ................... 606/20–26; 128/898; 607/103–105

(56) References Cited

U.S. PATENT DOCUMENTS

| | | | |
|---|---|---|---|
| 3,220,414 A | | 11/1965 | Johnston |
| 5,078,713 A | * | 1/1992 | Varney .................... 606/23 |
| 5,334,181 A | | 8/1994 | Rubinsky et al. |
| 5,433,717 A | * | 7/1995 | Rubinsky et al. ............ 606/20 |
| 5,452,582 A | * | 9/1995 | Longsworth ................ 62/51.2 |
| 5,520,682 A | * | 5/1996 | Baust et al. .................. 606/24 |
| 5,649,936 A | * | 7/1997 | Real ........................... 606/130 |
| 5,716,353 A | | 2/1998 | Matsuura et al. |
| 5,899,898 A | | 5/1999 | Arless et al. |
| 5,913,885 A | | 6/1999 | Klatz et al. |
| 5,916,242 A | | 6/1999 | Schwartz |
| 5,957,963 A | | 9/1999 | Dobak, III |
| 6,030,412 A | | 2/2000 | Klatz et al. |
| 6,041,787 A | * | 3/2000 | Rubinsky .................... 128/898 |
| 6,042,579 A | | 3/2000 | Elsberry et al. |
| 6,045,532 A | | 4/2000 | Eggers et al. |
| 6,051,019 A | | 4/2000 | Dobak, III et al. |
| 6,083,166 A | * | 7/2000 | Holdaway et al. .......... 600/439 |
| 6,096,068 A | * | 8/2000 | Dobak, III et al. ......... 607/105 |
| 6,106,518 A | | 8/2000 | Wittenberger et al. |
| 6,126,684 A | | 10/2000 | Gobin et al. |
| 6,149,677 A | | 11/2000 | Dobak, III et al. |
| 6,245,095 B1 | * | 6/2001 | Dobak, III et al. ......... 607/105 |
| 6,248,126 B1 | | 6/2001 | Lesser et al. |
| 6,386,202 B1 | | 5/2002 | Frazee |
| 6,413,263 B1 | * | 7/2002 | Lobdill et al. .............. 606/129 |

FOREIGN PATENT DOCUMENTS

WO       WO 01/76517 A2     10/2001

OTHER PUBLICATIONS

Cooper, I.S., *Cryogenic Surgery of the Basal Ganglia JAMA*, Aug. 1962; 181(7):600–604.

Cooper, IS. and Stellar, S., *Cryogenic Freezing of Brain Tumors for Excision or destruction in situ J Neurosurgery*, 1963; 20:921–930.

(List continued on next page.)

*Primary Examiner*—Michelle Peffley
(74) *Attorney, Agent, or Firm*—Christopher & Weisberg, P.A.

(57) ABSTRACT

A method is disclosed for treating brain tissue with cryotreatment. A surgical tool, such as a catheter is disposed proximate to a target region of brain tissue. The tool or catheter provided includes a cryotreatment element. The cryotreatment element may be a cryochamber for enclosing the flow of a fluid refrigerant therein. The cryotreatment element is disposed at the situs of brain tissue to be treated, either through endovascular insertion, or via an opening in the cranium. A refrigerant flow within the cryochamber creates endothermic cooling with respect to the surrounding brain tissue, inducing hypothermia and forming iceballs proximate said tissue. The cooling may be reversible and non-permanent, or may be permanent leading to cell death, necrosis, apoptosis and/or surgical excision or ablation of tissue. Mapping using conventional techniques may be used to measure and assess brain function before and after cryotreatment, and cryotreatment itself may be integrally and progressively used to map brain function and treat tissue.

14 Claims, 1 Drawing Sheet

OTHER PUBLICATIONS

Hill, M.W. et al., *Rapid Cooling Aborts Seizure–Like Activity in Rodent Hippocampal–Entorhinal Slices Epilepsia*, May 2000; 41(10): 1241–8.

Jerva, M.J., *Current Concepts of Cryoneurosurgery Proc Inst Med Chgo*, 1974 Jul.; 30:149–150.

Kindt, G.W., et al., *Cryosurgery for Parkinsonism and Other Abnormal Movement Disorders The Journal of the South Carolina Medical Association*, May 1967; 175–177.

Liu, Z., et al., *Effect of Temperature on Kainic Acid–Induced Seizures Brain Research*, Jul. 1993; 631:51–58.

Maroon, J.C., et al. *Cryosurgery Re–Visited for the Removal and Destruction of Brain, Spinal and Orbital Tumors Neurol Res*, 1992; 14:294–302.

Richardson, A., *Cryosurgery in Neurosurgery British Journal of Hospital Medicine*, Jul. 1975 39–46.

Tacke, J., *Thermal Therapies in Interventional MR Imaging—Cryotherapy Neuroimaging Clin N AM*, Nov. 2001; 11(4):759–65.

Tacke, J., et al., *Experimental MR Imaging–Guided Interstitial Cryotherapy of the Brain AJNR AM J Neuroradiol*, Mar. 2001; 22(3):431–40.

Yang, X.F., et al., *Neocortical Seizure Termination by Focal Cooling: Temperature Dependence and Automated Seizure Detection Epilepsia*, Dec. 2001; 43(3):240–245.

Zhou, L., et al., *Mechanism Research of Cryoanalgesia Neurological Research*, Aug.1995; 17:307–311.

* cited by examiner

METHOD OF USING CRYOTREATMENT TO TREAT BRAIN TISSUE

CROSS-REFERENCE TO RELATED APPLICATION

This application is related to and claims priority to U.S. Provisional Application Ser. No. 60/269,566, filed Feb. 16, 2001, entitled DEVICE AND METHOD FOR USING CRYOGENIC ENERGY TO TREAT BRAIN TISSUE, the entirety of which is incorporated herein by reference.

STATEMENT REGARDING FEDERALLY SPONSORED RESEARCH OR DEVELOPMENT n/a

FIELD OF THE INVENTION

The present invention relates to a method for treatment of brain tissue, and, in particular, a method for treating brain tissue using cryotreatment.

BACKGROUND OF THE INVENTION

Disorders of the brain, such as epilepsy, tumors, cysts, or Parkinson's disease, are conventionally treated by drug therapy. Yet drug therapy carries a significant risk of complications and side effects, and must be carefully monitored over a period of time to find the precise dosage required. Additionally, drug therapy can cause potentially life-threatening low blood pressure conditions and side effects. Further, brain disorders such as stroke (hemorrhagic or embolic), vasospasm, and ischemia pose additional difficulties. Another option, angioplasties, while providing some relief, are not always useful and are difficult to position inside the complex structure of the brain. Moreover, many patients do not respond to such treatment and thus surgical excision of a target region of brain tissue, or "focus", becomes necessary.

Normally, only the portions of the brain responsible for the transmission of abnormal activity are targeted for resection or sectioning. Yet in all cases, there is a risk of removing small amounts of normal brain tissue which may be critical to normal functions such as speech, sensory perception, or motor control. Known conventional techniques which employ heat or hyperthermia can cause significant peripheral damage by denaturing proteins in the brain, leaving waste substances behind leading to serious complications. To prevent such surgical sequellae, mapping methods have been developed to be used in conjunction with any procedure. Prior to surgery, extensive mapping using electroencephalography (EEG), magnetic resonance imaging (MRI), positron emission tomography (PET), computed tomography (CT), or other means can generate a detailed map of the brain and is used to identify the target focus. Once the area is adequately mapped, and a target focus identified, treatment can proceed wherein such focus is ablated as desired.

However, current methods are still imperfect as complications can readily occur. Part of the reason is that the conventionally used ablation tool itself is "absolute." Once the target focus site is identified, the surgical excision is performed and the procedure is final. No correction is made for mapping errors, nor does it allow for continuous or "progressive" monitoring of the ablation process. Known ablation tools do not allow for enhanced mapping in conjunction with, and as an integral part of, the ablation process.

Therefore, it is desirable to have a method for treating brain tissue that is minimally invasive and does not cause peripheral damage to healthy tissue. Furthermore, it is desirable to provide an ablation method to treat brain tissue which is progressive, may be used in conjunction with known mapping techniques, allowing for continuous mapping during the ablation process.

SUMMARY OF THE INVENTION

A method is disclosed for treating brain tissue, including the steps of providing a surgical tool having a cryotreatment element, mapping a target region of said brain tissue, identifying a first focus for cryotreatment, positioning said cryotreatment element proximate said first focus, and treating said first focus with said cryotreatment element.

Another method is disclosed for treating a target region of brain tissue, including the steps of providing a catheter having a flexible body having at least one lumen, proximal and distal end portions, said distal end portion enclosing a thermally transmissive cryochamber in fluid communication with said at least one lumen, positioning said catheter to dispose said cryochamber proximate said target region of brain tissue, injecting a refrigerant fluid flow into the at least one lumen in said catheter body, and expanding said refrigerant fluid flow inside said cryochamber.

Still another method is disclosed for cooling brain tissue, including the steps of providing a thermally transmissive cryochamber in fluid communication with a flow of fluid refrigerant therein, positioning said cryochamber proximate said brain tissue, injecting said fluid refrigerant into said cryochamber to flow therein, and changing the thermodynamic properties of said fluid refrigerant flow inside said cryochamber to absorb heat from said brain tissue.

Finally, a method is disclosed for cryotreatment of brain tissue, comprising the steps of identifying a conduction path in a region of said brain tissue, and applying cryotreatment to said region of brain tissue to create a lesion in said tissue and to form a conduction block along a said conduction path.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
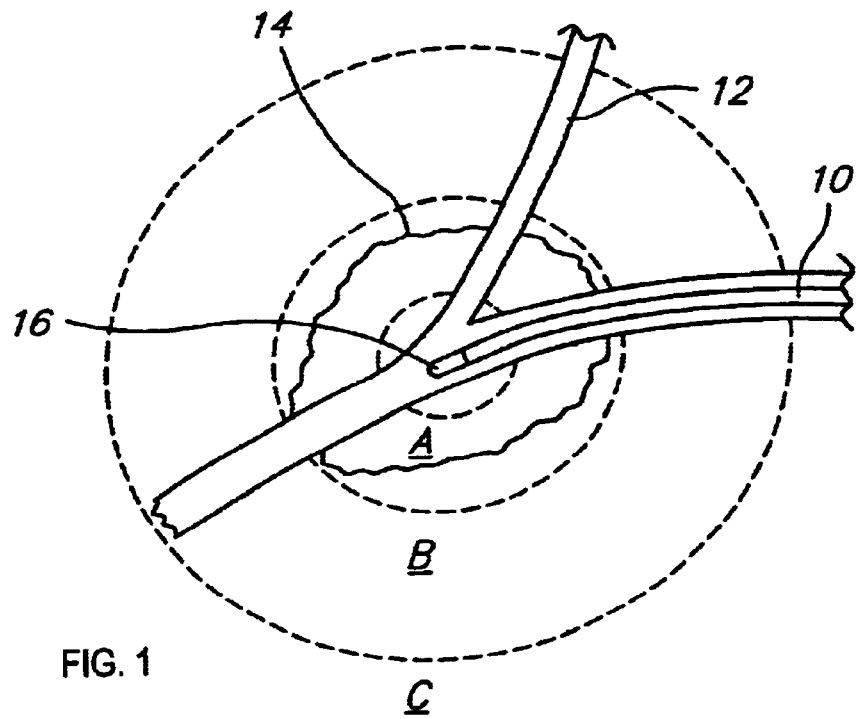
FIG. 1 is a view of a catheter with a cryotreatment element inserted endovascularly to be disposed proximate a target region of brain tissue.

As used herein, the term "target region" or "focus" shall mean a defined volume or mass of tissue, either in the brain or some other part of the human body. As used herein, the term "cryotreatment" shall mean the application of cold temperatures to cool body tissue, and shall include "cryoablation", which shall mean the application of cold temperatures to cool body tissue to such a degree so as to cause cell death, necrosis, or apoptosis in said tissue, or to otherwise surgically remove such tissue. Accordingly, as used herein, the term "treating" shall mean cooling or ablating.

As used herein, the term "mapping" shall mean the use of medical imaging and other diagnostic techniques to measure and monitor body functions and physiological parameters, such as electrical activity in tissue. As used herein, the term "remapping" shall mean conducting mapping after an initial round of mapping and some ancillary diagnostic or surgical procedure has been initiated, as also used to describe the process of "progressive mapping", which shall mean the use of mapping in conjunction with a surgical procedure, as may be done in real time. As used herein, "chemotherapeutic agents" shall mean certain drugs, chemicals, or substances, such as apoptosis enhancers, used to accelerate the effects of cryotreatment. As used herein, the term "cryoprotectant agents" shall mean certain drugs, chemicals, or substances, such as caspase (apoptosis) inhibitors, which neutralize or counteract the effects of cryotreatment.

Cryotreatment entails applying cold temperatures to specific regions of the body. Such "cold energy" can be safely and effectively used to treat a host of medical conditions by creating endothermic heat transfer from a surgical tool relative to a region of tissue, so as to induce hypothermia and cause such tissue to be cooled. Unlike heat-based technologies that destroy tissue structure, the application of cryotreatment preserves structural integrity. This benefit is achieved by selectively destroying the cellular components through intra- and inter-cellular ice formation while leaving the connective tissue matrix intact. In addition, cryotreatment shows potential to greatly minimize one of the most harmful side effects of heat-based treatments: thrombosis, or blood clot formation, which can lead to stroke. As a further advantage, cryotreatment affords the clinical practitioner effective and precise control of multiple operating parameters, such as iceball position, shape, size, and growth rates, tissue temperature, and cooling duration.

The cooling of tissue may be accomplished by disposing a cooling element proximate said tissue. The element may be fitted onto a variety of surgical tools. For applications which require minimally invasive techniques, the cooling element may be disposed onto a slender catheter which is then positioned through brain vasculature near or at the situs of tissue to be cooled. The catheter may contain one or more lumens therein, adapted to contain the flow of a liquid or gaseous fluid refrigerant therein. The fluid refrigerant is thereafter thermodynamically manipulated inside a "cryochamber." A cryochamber may be generally described as a defined, enclosed volume within the catheter, whereby, for example, the refrigerant flow may be expanded from high to low pressure, such as through a Joule-Thomson throttling process, to create endothermic heat transfer with respect to its surroundings. This heat transfer, when spatially directed to a target region of tissue will act to cool said tissue by absorbing heat from said tissue into the cryochamber and flow of refrigerant therein. The cryochamber is preferably thermally transmissive, having structural components which readily conduct heat. The cryochamber may also be electrically conductive, having elements which readily conduct electric charge. Examples of materials preferentially used to construct such a cryochamber are polymers, plastics, non-ferrous metals such as gold or copper, or a mixture thereof.

The refrigerant used may be any number of fluids suitable for stable compression to pressures on the order of 10 psig to up to 6000 psig. Preferential examples of such fluids are nitrous oxide ($N_2O$), nitrogen ($N_2$), argon, or AZ-20. Catheters may be flexible or rigid, constructed of a variety of materials, including plastics and both ferrous and non-ferrous metals, and would preferably have diameters on the order of 2 to 7 French.

FIG. 1 illustrates an embodiment of one method by which a catheter 10 is inserted into a vascular system 12 proximate a target region of tissue 14 in the brain. The catheter 10 contains a cryotreatment or cryoablation element 16 located at its distal tip. The cryotreatment element 16 further includes a cryochamber therein (not shown) whereby a flow of refrigerant fluid is thermodynamically manipulated or cycled to cool the surrounding environment, that being the target tissue region 14. An example of the thermodynamic process may be gas expansion through Joule-Thomson cooling, or evaporation of the refrigerant from liquid to gaseous phase, or both. It is readily understood that catheter 10 includes one or more lumens disposed along its length (not shown) which carry the flow of refrigerant from a source or supply coupled to the catheter's proximal end, to the cryotreatment element 16, and then back through the catheter, either in a closed loop arrangement where refrigerant is recycled through the system and recaptured, or an open loop system wherein refrigerant is vented from the system without recapture. For certain applications, an arrangement may be used where a substance, being preferably non-toxic or inert, is injected by the catheter into the tissue region 14. One example of such a use would be that of injecting drugs or other therapeutic agents either in conjunction with, or independent of, the cooling of tissue via the cryotreatment element 16.

As refrigerant flows through the catheter 10, and cooling is progressively applied, the size of the iceballs, and/or isotherms in the case of warmer, non-freezing cryotreatment, formed in and around the target tissue region 14 grows in size, as illustrated by the successively larger circles A, B, and C shown in FIG. 1. Although such iceballs or isotherms are shown as circular in FIG. 1, it is readily understood that varying shapes may be formed, having linear, cylindrical, ellipsoidal, toroidal, or curved topologies.

The method described above may also be used in conjunction with a known mapping system. The brain is mapped using conventional methods such as MRI, CT scan, PET scan, ultrasound, EEG, or the like. The critical regions of the brain are studied and analyzed via such mapping, so that specific target areas of brain tissue are identified for cryotreatment. Such areas may be foci responsible for epilepsy or other neurological disorders such as Parkinson's disease, or may be defined tissue structures such as tumors and cysts. The cooling of target brain tissue 14 may either temporarily or permanently interrupt electrical activity proximate such brain tissue. The resulting effects on the entire body may then be measured, as with the mapping techniques outlined above. This method may be incorporated into a "progressive mapping" scheme, whereby specific brain regions are mapped; cryotreatment is applied; the regions are again mapped or "remapped"; the effects of the cryotreatment are evaluated; and, if necessary, additional cycles of mapping and cryotreatment are executed until the desired results are achieved. Thoughout the process, the tissue may be neither destroyed nor removed. In this sense therefore, cryotreatment and "cryomapping" allow for real-time, feedback oriented treatment of brain tissue, wherein such treatment is reversible and non-permanent. Furthermore, catheters constructed in accordance with the present invention, such as with polymers or nonferrous metals, are compatible with most mapping devices like MRIs and CTs.

Indeed, as opposed to ablation, whereby the cooling applied to brain tissue is permanent and destroys a portion of such tissue, the cooling may be relatively short and reversible, whereby the cryotreatment of a specific target region of brain tissue temporarily inhibits the electrical activity in such brain tissue to test the effects of a proposed ablation prior to performing the permanent ablation. This method may thus be used to test specific functionalities of areas of the brain without doing undue permanent damage to cells or cell structures.

Furthermore, a method may be employed wherein cryotreatment is used to cool regions of healthy brain tissue, by first identifying a conduction path in a region of said brain tissue, and then applying cryotreatment to said region of brain tissue to create a lesion (damaged tissue) in said tissue and to form a conduction block along said conduction path.

The nature of cryotreatment and the extent of cooling applied to brain tissue, such as target region 14 shown in FIG. 1, may vary widely with the application and medical condition at issue. One example of a disorder affecting brain tissue is vasospasm, a narrowing of the arteries supplying oxygen and nutrients to the brain, which has been identified in patients having undergone hemorrhagic stroke events. Other diseases associated with vasospasm include headaches, stroke, brain injuries, post-concussion syndrome, whiplash, balance disorders, vertigo, attention deficit disorder, seizures, pseudo-seizures, dyslexia, visual blurring, depression, psychosis, movement disorders, tremor, memory loss, angina, fibromyositis, toxemia and pre-eclampsia, cognitive disorders including chemical allergies and medications, among others. The method may also be applied to counteract the stenosis caused by vasospasm, wherein cryotreatment is applied in the affected vascular vessels and interior walls of the smooth muscle lining of such vessels. The applied cold immediately causes vascular relaxation, thereby reducing the vasospasm and restoring critical blood flow for brain functioning. The method may also be applied to non-neurological sites and the general vascular system, such as arteries affected by arteriosclerosis, ranging in size from 1.0 to 6.0 mm, or other arteries that are stenotic and/or difficult to treat with a conventional stent.

It is known that tissue cooling may also be applied to slow down metabolic function in the target region of brain tissue to limit the damage following an ischemic stoke, such as described in U.S. Pat. Nos. 6,149,677, 6,096,068, 6,042,559. The catheter 10 may be inserted into the ischemic tissue of the brain to cool such tissue to a temperature which promotes angiogenic response. Such temperatures are preferably below zero degrees Celsius, but may also be in the range above freezing and below body temperature, so as to further enhance the angiogenic response while minimizing the danger to the brain tissue. The method may furthermore be used to induce angiogenesis in any desired target region of brain tissue, regardless of the particular medical condition at issue.

Figure 2:
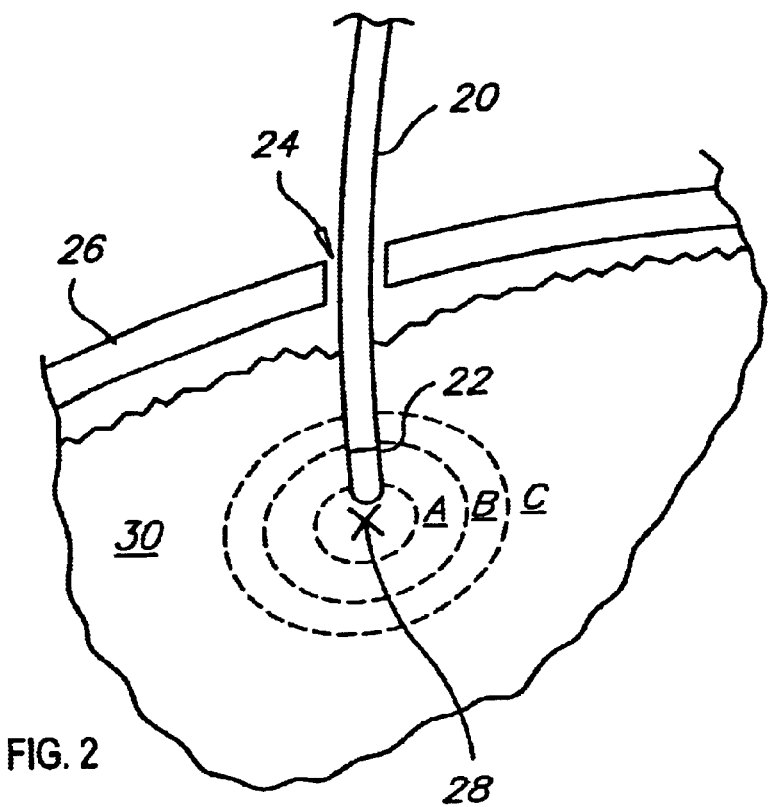
FIG. 2 is a view of a surgical tool with a cryotreatment element disposed through an opening in the cranium to be disposed proximate a target region of brain tissue.

FIG. 2 shows an alternative method by which a target region of brain tissue may be treated via cryotreatment. FIG. 2 illustrates an elongate surgical tool 20 having a cryotreatment element located at its distal tip 22, inserted through an opening or pathway 24, such as a "burr-hole", through the cranium 26, and disposed proximate a focus or target site 28 in the brain 30. Cryotreatment is used to cool such focus 28, so that varying degrees of cooling are achieved in and around such focus 28. The circles of successively increasing diameter, labeled as A, B, and C in FIG. 2, represent the spatial progression of such cooling, and may be indicative of the relative size of iceballs created, or may represent the isotherms around the focus 28 as cryotreatment is applied. This method may also be employed with the above-described mapping techniques so as to provide a more precise, interactive and real-time capability in identifying the regions of brain tissue to be treated; applying cryotreatment based on such determinations; analyzing the results and effects of cryotreatment; and recursively repeating such process until the desired clinical goals are achieved.

Cryotreatment as used in either of the methods described above may generate a widely varying range of tissue temperatures. Tissue temperatures in the range of +30 to −40 degrees Celsius may be used to cause a reversible interruption of electrical activity in either normal or diseased brain tissue. This range may also be used with mapping techniques to confirm the effects of cryotreatment and to assess brain function. Tissue temperatures in the range of +20 to −200 degrees Celsius may be used to cause permanent interruption of electrical activity, cell death, necrosis, or apoptosis in some or all of the tissues surrounding the target region of tissue. Such cell death may occur as a result of direct freeze injury, via intra- or extra-cellular ice formation, or through indirect injury, such as dessication, ischemia, or inflammation.

Also, cryotreatment may cause thrombosis of small arteries and capillaries in the target region thereby reducing hemorrhage associated with conventional excision of tissue. This effect may also increase ischemia and/or cell death in the target tissue.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for treating a target region of brain tissue, comprising the steps of:
   providing a catheter having
      a flexible body having
         at least one lumen,
         proximal and distal end portions, said distal end portion enclosing a thermally transmissive cryochamber in fluid communication with said at least one lumen,
   positioning said catheter to dispose said cryochamber proximate said target region of brain tissue,
   injecting a refrigerant fluid flow into the at least one lumen in said catheter body, and
   expanding said refrigerant fluid flow inside said cryochamber,
   wherein the step of positioning said catheter to dispose said cryochamber proximate said target region of brain tissue comprises:
      percutaneously inserting said distal end portion of said catheter in a vascular pathway connected to said target region of brain tissue, and
      advancing said catheter through said pathway to dispose said cryochamber proximate said target region of brain tissue.

2. The method of claim 1, further comprising the steps of:
   mapping the target region of brain tissue,
   identifying a first focus for cryotreatment,
   positioning said cryochamber proximate said first focus, and
   treating said first focus with said cryochamber.

3. The method of claim 1, wherein said first focus is an epileptic focus.

4. The method of claim 1, wherein said cryotreatment comprises cryoablation and said step of treating said first focus comprises ablating said first focus.

5. The method of claim 1, wherein said treating of said first focus comprises cooling said brain tissue proximate said first focus to a predetermined temperature.

6. The method of claim 5, wherein said predetermined temperature is in a subrange in the range of +30 to −200 degrees Celsius.

7. The method of claim 6, wherein said subrange is +30 to −40 degrees Celsius, and said cooling of said brain tissue proximate said first focus comprises causing reversible interruption of electrical activity of at least part of said brain tissue proximate said first focus.

8. The method of claim 6, wherein said subrange is +20 to −200 degrees Celsius, and said cooling of said brain tissue proximate said first focus comprises causing permanent interruption of electrical activity of at least part of said brain tissue proximate said first focus.

9. The method of claim 6, wherein said subrange is +20 to −200 degrees Celsius, and said cooling of said brain tissue proximate said first focus comprises causing necrosis of at least part of said brain tissue proximate said first focus.

10. The method of claim 6, wherein said subrange is +20 to −40 degrees Celsius, and said cooling of said brain tissue proximate said first focus comprises causing apoptosis of at least part of said brain tissue proximate said first focus.

11. The method of claim 6, wherein said subrange is +20 to −200 degrees Celsius, and said first focus is an epileptic focus.

12. The method of claim 1, further comprising the steps of:

remapping said target region of brain tissue, identifying an additional focus, if any, for cryotreatment, positioning said cryochamber proximate said additional focus, and treating said additional focus with said cryochamber, wherein the foregoing steps are repeatedly performed until no additional focus is identified.

13. The method of claim 1, further comprising the step of infusing chemotherapeutic agents into said brain tissue proximate said first focus to potentiate said treating of said first focus with said cryochamber.

14. The method of claim 1, further comprising the step of infusing cryoprotectant agents into said brain tissue proximate said first focus.

* * * * *